United States Patent [19]

Shawl

[11] 4,162,362

[45] Jul. 24, 1979

[54] PROCESS FOR THE PREPARATION OF DIPHENYLMETHANE DICARBAMATES AND POLYMETHYLENE POLYPHENYL CARBAMATES

[75] Inventor: Edward T. Shawl, Wallingford, Pa.

[73] Assignee: Atlantic Richfield Company, Los Angeles, Calif.

[21] Appl. No.: 953,135

[22] Filed: Oct. 20, 1978

[51] Int. Cl.$^2$ ............................................. C07C 125/04
[52] U.S. Cl. ....................................... 560/25; 528/242; 528/266
[58] Field of Search ........................................... 560/25

[56] References Cited

U.S. PATENT DOCUMENTS

| 2,946,768 | 7/1960 | Klauke et al. | 260/453 P |
| 3,919,279 | 11/1975 | Rosenthal et al. | 260/453 P |
| 3,962,302 | 6/1976 | Rosenthal et al. | 260/453 P |
| 4,014,914 | 3/1977 | Pistor et al. | 260/570 D |

FOREIGN PATENT DOCUMENTS 461352  2/1937  United Kingdom ..................... 560/25

*Primary Examiner*—Bernard Helfin
*Assistant Examiner*—G. T. Breitenstein
*Attorney, Agent, or Firm*—Delbert E. McCaslin

[57] ABSTRACT

Diphenylmethane dicarbamates and polymethylene polyphenyl carbamate homologs and derivatives of these compounds are produced by the condensation of N-aryl carbamic acid esters, such as ethylphenylcarbamate, with formaldehyde, para-formaldehyde or trioxane in the presence of an organic sulfonic or halogenated organic sulfonic acid which has an acid concentration of at least 75 percent, at temperatures of from ambient to about 170° C. and optionally in the presence of an inert solvent.

13 Claims, No Drawings

PROCESS FOR THE PREPARATION OF DIPHENYLMETHANE DICARBAMATES AND POLYMETHYLENE POLYPHENYL CARBAMATES

FIELD OF THE INVENTION

The present invention relates to a process for the preparation of esters of aromatic carbamic acids (urethanes) particularly diphenylmethane dicarbamates and related higher homologs and derivatives by condensation of N-aryl carbamic acid esters with carbonyl compounds in the presence of organic or halogenated organic sulfonic acids.

BACKGROUND OF THE INVENTION

Polymeric aromatic carbamic acid esters (polyurethanes) such as diphenylmethane dicarbamates and the related higher homologs polymethylene polyphenyl carbamates have become increasingly important products, particularly for use in the preparation of the commercially valuable diphenylmethane diisocyanates and mixtures of diisocyanates and polyisocyanates by the decomposition of such polymeric aromatic carbamic acid esters in a suitable solvent as shown, for example, in Rosenthal et al, U.S. Pat. Nos. 3,962,302 and 3,919,279.

At the present time there is no known successful commercial method for the direct preparation of polymeric aromatic esters of carbamic acid. The corresponding diphenylmethane diisocyanates and polyisocyanates, available commercially, are largely produced by the phosgenation of mixtures of diamines and polyamines obtained by the condensation of aniline and formaldehyde with catalytic quantities of a mineral acid, as for example, disclosed in the Pistor et al, U.S. Pat. No. 4,014,914.

Prior art processes have been proposed for the preparation of polymeric aromatic carbamic acid esters (polyurethanes) as for example in Klauke et al, U.S. Pat. No. 2,946,768 and British Pat. No. 461,352 which disclose the condensation of aryl carbamic acid esters with carbonyl compounds such as aldehydes and ketones in a dilute aqueous mineral acid condensation medium. In such processes the carbonyl compound such as formaldehyde tends to react at the nitrogen of the carbamate to produce along with some desired polyurethanes, varying amounts, i.e., generally between 15 percent and 50 percent by weight, of undesirable N-(alkoxycarbonyl)phenylaminomethylphenyl compounds which include dimers, trimers, tetramers, etc. of such compounds, which compounds referred to as N-benzyl compounds are fully described in co-pending allowed U.S. application, Ser. No. 905,705, filed May 15, 1978. Attempts to prepare diisocyanates and polyisocyanates or to otherwise use the mixture containing the polyurethanes and such amounts of the undesired compounds, which compounds cannot be converted to an isocyanate by pyrolysis, presents many problems since there is no known method for separating the polyurethanes from the N-(alkoxycarbonyl)phenylaminomethylphenyl impurities.

The present invention which comprises the preparation of diphenylmethane dicarbamates and polymethylene polyphenyl carbamate homologs and derivatives of these compounds by the condensation of N-aryl carbamic acid esters with formaldehyde, para-formaldehyde or trioxane in the presence of an organic sulfonic acid which has an acid concentration of at least 75 percent substantially avoids the above mentioned problem and the formation of such impurities.

The organic sulfonic acids employed in the process of this invention are superior catalysts for the condensation of the N-aryl carbamates for a number of reasons. (1) Containing organic substituents the sulfonic acids are generally more soluble in the carbamate solution than the mineral acids thus providing a single phase reaction at the operable concentrations. (2) The organic sulfonic acids which are strong acids substantially eliminate formation of the N-(alkoxycarbonyl)phenylaminomethylphenyl impurities during condensation. (3) Undesirable side reactions such as sulfonation of the N-aryl carbamates and chlorination which occur with sulfuric and hydrochloric acid for example, are avoided. Since these side reactions are suppressed, a higher quality diphenylmethane dicarbamate and polymethylene polyphenyl carbamate product is obtained which upon pyrolysis to the polymeric aromatic isocyanate gives a higher isocyanate yield.

SUMMARY OF THE INVENTION

This invention relates to a process for the preparation of diphenylmethane dicarbamates and the higher molecular weight homologs, polymethylene polyphenyl carbamates, which comprises condensing an N-aryl carbamic acid ester with a carbonyl compound such as formaldehyde, para-formaldehyde or trioxane or mixtures thereof in the presence of an organic sulfonic or halogenated organic sulfonic acid which has an acid concentration of at least 75 percent.

It is an object of the present invention therefore to provide a process for the preparation of diphenylmethane dicarbamates and the related polymethylene polyphenyl carbamates in high yield by the condensation of an N-aryl carbamic acid ester with a carbonyl compound in the presence of an organic sulfonic acid.

It is another object of this invention to provide a process for the condensation of N-aryl carbamic acid esters with formaldehyde, para-formaldehydes or trioxane in the presence of a strong organic sulfonic acid or halogenated sulfonic acid and substantially avoiding the problems associated with the employment of mineral acids.

These and other objects and advantages of this invention will become apparent from the description of the invention which follows and from the claims.

DESCRIPTION OF THE INVENTION

In accordance with the present invention an aromatic carbamic acid ester (N-arylcarbamic acid ester) such as, for example, a lower alkyl ester of phenyl carbamic acid, particularly ethyl phenyl carbamate, is contacted with formaldehyde, para-formaldehyde or trioxane at a temperature of from about ambient to about 170° C., preferably under atmospheric pressure, with or without the addition of an inert solvent, in the presence of an organic sulfonic acid catalyst comprising alkane sulfonic acids, halogenated alkane sulfonic acids or aromatic sulfonic acids to give a reaction product mixture of diphenylmethane dicarbamates and polymethylene polyphenyl carbamates.

The organic sulfonic acid catalyzed reaction may be carried out in any suitable reactor which is generally equipped with a means for agitation and a means for regulating temperature. A general procedure for carrying out the reaction is to charge the N-aryl carbamic acid ester and optionally a solvent into the reaction vessel together with the desired carbonyl compound, e.g., formaldehyde, and the sulfonic acid catalyst and then heat or cool the mixture, if necessary, to the desired reaction temperature for the appropriate period. Heating and/or cooling means may be employed interior and/or exterior of the reaction to maintain the temperature within the desired range. The reaction may be carried out as a batch, semicontinuous or a continuous process and the order of addition of the materials may be varied to suit the particular apparatus employed. The reaction products are recovered and treated by any conventional method such as extraction of the acid medium with water or neutralization with an appropriate inert base and the separation of the resulting phases, as well as distillation to remove any solvent employed.

The N-aryl carbamic acid esters employed as reactants in the acid catalyzed condensation reaction must contain one or more carbamic acid ester groups, i.e. —NHCOOR groups, wherein R is an alkyl group containing up to 8 carbon atoms, an aryl group or alkyl substituted aryl group having up to 4 carbon atoms in the alkyl substituent. The N-aryl group of the carbamic acid ester may also contain substituents such as alkyl, alkoxy, halogen, etc. on the ring. The lower alkyl esters, e.g., ethyl esters such as ethyl phenyl carbamate are preferred. The N-aryl carbamic acid esters for use in the invention may be prepared for example by the process disclosed in Zajacek et al U.S. Pat. No. 3,895,054 wherein the carbamic acid esters (urethanes) are prepared by reacting an organic compound containing at least one hydroxyl group with carbon monoxide and a nitrogenous organic compound at elevated temperature and pressure in the presence of a selenium catalyst and a base and/or water, or by any other known process for preparing aromatic carbamates.

The carbonyl compounds which may be employed in the process of the invention are formaldehyde or paraformaldehyde and trioxane which are capable of producing monomeric formaldehyde in the presence of acid. The quantity of the carbonyl compound employed in the reaction relative to the N-aryl carbamic acid ester employed is based on the degree of condensation or polymerization desired in the reaction product. Generally, the molar ratio of N-aryl carbamic acid ester to the carbonyl compound, in the form of free formaldehyde in the reaction mixture, will be in the range of about 1.5 to 8:1. At the high end of the range the production of dimeric carbamates will predominate whereas at the low end of the range the higher polymeric polymethylene polyphenyl carbamates will predominate.

The organic sulfonic acid medium employed as condensation catalyst and suitable for use in the present invention may be an alkane sulfonic acid or a halogenated alkane sulfonic acid having for example, up to 10 carbon atoms in the alkyl group, or an aromatic sulfonic acid. Mixtures of the sulfonic acid catalysts may be employed but it is preferable to use an individual acid catalyst in order to lessen any recovery problems. Representative organic sulfonic acid catalysts especially suitable for use in this invention are methane, ethane, butane, etc. sulfonic acids, trifluoromethane sulfonic acid, trichloromethane sulfonic acid, p-toluene sulfonic acid, benzene sulfonic acid, etc. The organic sulfonic acids are generally employed in concentrations of from about 0.1 to 75 weight percent, preferably 5.0 to 50 weight percent of the N-aryl carbamate employed.

Although the process of the present invention may be carried out in the absence of solvents, particularly at the higher temperatures of reaction, i.e., 60° C. and above, solvents or mixtures of solvents which are stable and chemically inert to the components of the reaction system may be and are generally employed due to the viscosity of the condensed reaction product. Suitable solvents which may be employed generally in amounts of from 0 to 50 weight percent based on the reaction mixture include, for example, nitrated and halogenated aromatic hydrocarbons having up to 12 carbon atoms such as nitrobenzenes, nitrotoluenes, dichlorobenzene, dibromobenzene; alkanes and substituted alkanes, having up to 16 carbon atoms, such as n-pentanes, isopentane, n-hexane, 2-methylpentane, n-heptane, 3,4-dimethylhexane, 2-methylhexane, 3-ethylpentane, cyclopentane, cyclohexane, methylcyclohexane, ethylcyclopentane, cyclooctane, chloroform, carbon tetrachloride, dichloroethane, etc.; lower aliphatic acids having up to 8 carbon atoms, such as acetic, propionic, etc., and lower aliphatic alcohols, having up to 8 carbon atoms, such as methanol, ethanol, propanols, butanols, etc. Nitrobenzene and dichlorobenzene are the preferred solvents. Greater amounts of solvent may be employed but generally are not necessary due to the added burden of recovery. While as indicated above, mixtures of solvents may be employed, it is preferable to use individual solvents in order to alleviate any recovery problem.

The reaction of the present invention will proceed at temperatures of from ambient to 170° C. It is generally preferred to operate the process at temperatures of from about 50° C. to 130° C. to obtain a convenient rate of reaction.

The process of the present invention is generally carried out at atmospheric pressure although higher pressures may be used at the higher reaction temperatures. Subatmospheric pressures may also be employed in the process, if desirable.

The reaction time is generally dependent upon the N-aryl carbamate being reacted, the reaction temperature and on the amount and type of sulfonic acid catalyst being employed and will vary depending on whether the process is continuous or batch but will generally range between about 2 minutes and several hours.

The following Examples are provided to illustrate the invention in accordance with the principles of this invention but are not to be construed as limiting the invention in any way except as indicated by the appended claims.

In the Examples which follow, the reactions were run in a 300 ml. or appropriate size three neck glass reaction flask fitted with a mechanical stirrer, reflux condenser and thermometer. The reactants were charged to the reaction flask and the flask immersed into a constant temperature oil bath. At the end of the reaction time, water was added to the flask to quench the reaction and extract the sulfonic acid catalyst medium. The condensate was washed with additional water or a 1 Normal solution of sodium hydroxide was added to neutralize any residual acid and solvent, if present was removed by distillation. Conversion of the N-aryl carbamate charged and condensation product yield and polymer distribution were determined by high speed liquid chromatography.

EXAMPLE 1

A solution of 12.1 g. of trioxane in 24.2 g. of nitrobenzene was added over a 25 minute period to a mixture of 120 g. of ethylphenylcarbamate, 120 g. of nitrobenzene, and 52 g. of trifluoromethane sulfonic acid. External cooling was used to maintain the temperature at 25° C. during the trioxane addition. The mixture was stirred at 25° C. for another 20 minutes and then it was heated to 70° C. for 45 minutes. The resulting product contained only a trace amount (<1%) of N-(alkoxycarbonyl)-phenylaminomethylphenyl impurities. Conversion of the ethylphenylcarbamate was 91 percent. The product was a mixture of the diphenylmethane dicarbamates (~50%) and higher polymeric carbamates (polymethylene polyphenyl carbamates). The isocyanate product isolated after pyrolysis of the carbamates contained 31 percent isocyanate groups by weight.

EXAMPLES 2 TO 15

In Examples 2 to 15, which follow in Table form, the general procedure of Example 1 was repeated using various N-aryl carbamates sulfonic acid catalysts, solvents, and reaction conditions. In Examples 2, 3 and 4 the acid catalyst was added over 20, 10 and 5 minute periods respectively, to a mixture of carbonyl compound, carbamate and solvent initially at a temperature of 25° C. In Examples 5–15 the reactants, solvent, if any, and acid were all mixed together and the resulting exotherm and reaction mixture controlled at the reaction temperature for the desired period.

TABLE

| Ex. No. | 1 | 2 | 3 | 4 | 5 | 6 | 7 | 8 | 9 | 10 |
|---|---|---|---|---|---|---|---|---|---|---|
| 2 | $CF_3SO_3H$ (40g) 99 wt. % | 51% aqueous formaldehyde (15.6) | $EPC^{(1)}$ 120 | Nitrobenzene (120) | 80 | 40 | 82 | 53 | 3 | 96 |
| 3 | $CH_3SO_3H$ (80g) 99 Wt. % | Trioxane (10.4) | EPC 120 | Nitrobenzene (120) | 80 | 40 | 80 | 56 | 0 | 99 |
| 4 | $CH_3SO_3H$ (40g) 99 wt. % | Trioxane (10.4) | EPC 120 | Nitrobenzene (120) | 95 | 45 | 83 | 51 | 2 | 97 |
| 5 | $CF_3SO_3H$ (3g) 99 wt. % | Paraformaldehyde (.38) | EPC 6 | Nitrobenzene (6) | 60 | 60 | 60 | 73 | <1 | 98 |
| 6 | $CF_3SO_3H$ (0.75g) 99 wt. % | Paraformaldehyde (.38) | EPC 6 | Nitrobenzene (6) | 100 | 30 | 61 | 66 | 0.2 | 99 |
| 7 | p-toluene $SO_3H \cdot H_2O$ (3.75g) 90.5 wt. % | Paraformaldehyde (0.38) | EPC 6 | Nitrobenzene (6) | 120 | 30 | 55 | 60 | 0 | 99.5 |
| 8 | $CH_3SO_3H$ (2g) 98 wt. % | Paraformaldehyde (0.38) | EPC 6 | Nitrobenzene (6) | 100 | 30 | 60 | 70 | .1 | 98 |
| 9 | $CH_3SO_3H$ (60g) 99 wt. % | Trioxane (7.8) | EPC 90 | None | 80 | 50 | 79 | 50 | 0 | 99.5 |
| 10 | $CF_3SO_3H$ (60g) 80 wt. % | Trioxane (5.2) | EPC 60 | Nitrobenzene (60) | 80 | 90 | 80 | 59 | 0 | 99.5 |
| 11 | $CH_3SO_3H$ (47.0g) 99 wt. % | Trioxane (7.8) | EPC 60 | Nitrobenzene (60) | 80 | 50 | 94 | 35 | 0.1 | 99 |
| 12 | $CF_3SO_3H$ (1.5g) 90 wt. % | Paraformaldehyde (0.38) | $BPC^{(2)}$ 7 | 1,2-dichloroethane (7) | 60 | 120 | 80 | 55 | 1.5 | 97 |
| 13 | $CF_3SO_3H$ (1.5g) 99 wt. % | Trioxane (0.38) | $EMPC^{(3)}$ 6.5 | o-dichlorobenzene (6.5) | 80 | 50 | 80 | 58 | 0.2 | 98 |
| 14 | $C_2H_5SO_3H$ (4g) 96 wt. % | Trioxane (0.38) | $MPC^{(4)}$ 5.5 | Nitrobenzene (5.5) | 80 | 60 | 80 | 55 | 1.0 | 98 |
| 15 | $CF_3SO_3H$ (60g) 99 wt. % | Trioxane (5.2) | EPC 120 | Nitrobenzene (120) | 30 | 240 | 81 | 59 | 2.3 | 96.5 |

Footnotes
(1)EPC - Ethylphenyl carbamate
(2)BPC - 1-butyl-N-phenylcarbamate
(3)EMPC - Ethyl-N-(2-methylphenyl)carbamate
(4)MPC - Methyl-N-phenylcarbamate
COLUMN HEADINGS
1 - Acid Catalyst (g) and Weight Per cent
2 - Carbonyl Compound (g)
3 - N-aryl Carbamate (g)
4 - Solvent (g)
5 - Temperature (°C.)
6 - Time (min.)
7 - Wt. % N-arylcarbamate Conversion
8 - Wt. % Diphenylmethane Dicarbamate in Product
9 - Wt. % N-(alkoxycarbonyl) Impurities
10 - Wt. % Dimer and Higher Polymers

I claim:

1. A process for the preparation of diphenylmethane dicarbamates and polymethylene polyphenyl carbamates which comprises reacting an N-aryl carbamic acid ester with a carbonyl compound selected from formaldehyde, para-formaldehyde or trioxane or mixtures thereof, at a temperature of from ambient to about 170° C. in the presence of an organic sulfonic acid catalyst medium selected from alkane sulfonic acids, halogenated alkane sulfonic acids or aromatic sulfonic acids which have an acid concentration of at least 75 percent and recovering the desired carbamates.

2. A process according to claim 1 wherein the N-aryl carbamic acid ester is selected from the group consisting of ethylphenylcarbamate, 1-butyl-N-phenylcarbamate, ethyl-N-(2-methylphenyl)carbamate and methyl-N-phenyl-carbamate.

3. A process according to claim 2 wherein the carbamic acid ester is ethylphenylcarbamate.

4. A process according to claim 1 wherein the organic sulfonic acid catalyst medium is selected from the group consisting of trifluoromethane sulfonic acid, methane sulfonic acid, p-toluene sulfonic acid and ethane sulfonic acid.

5. A process according to claim 4 wherein the organic sulfonic acid catalyst medium is methane sulfonic acid.

6. A process according to claim 4 wherein the organic sulfonic acid catalyst medium is trifluoromethane sulfonic acid.

7. A process according to claim 1 wherein the organic sulfonic acid is employed in concentrations of from about 0.1 to 75 weight percent based on the N-aryl carbamate employed.

8. A process according to claim 1 wherein the molar ratio of N-aryl carbamic acid ester to carbonyl compound in the form of free formaldehyde in the reaction mixture is in the range of from about 1.5 to 8:1.

9. A process according to claim 1 wherein the reaction is carried out in the presence of an inert solvent selected from the group consisting of nitrated and halogenated hydrocarbons having up to 12 carbon atoms, alkanes and substituted alkanes having up to 16 carbon atoms, lower aliphatic acids and lower aliphatic alcohols having up to 8 carbon atoms.

10. A process according to claim 9 wherein the solvent is nitrobenzene, dichlorobenzene or dichloroethane.

11. A process according to claim 10 wherein the solvent is nitrobenzene.

12. A process according to claim 1 wherein the reaction is carried out at a temperature in the range of from about 50° C. to 130° C.

13. A process for the preparation of a diphenylmethane dicarbamate, diethyl ester, which comprises reacting at atmospheric pressure ethylphenyl carbamate with formaldehyde at a temperature of from about 50° C. to 130° C. in the presence of from 5.0 to 50 weight percent of the ethylphenyl carbamate employed of an organic sulfonic acid catalyst medium selected from the group consisting of trifluoromethane sulfonic acid, methane sulfonic acid, p-toluene sulfonic acid and ethane sulfonic acid which have an acid concentration of at least 75 percent, and a nitrobenzene solvent, and recovering the desired diphenylmethane dicarbamate.

* * * * *